United States Patent [19]

Takeuchi et al.

[11] 4,417,149
[45] Nov. 22, 1983

[54] APPARATUS FOR DETECTING AND MEASURING DEFECTS

[75] Inventors: Hideaki Takeuchi; Tsunehiko Takahashi; Masaru Noguchi, all of Asaka, Japan

[73] Assignee: Fuji Photo Film Co., Ltd., Tokyo, Japan

[21] Appl. No.: 303,684

[22] Filed: Sep. 18, 1981

[30] Foreign Application Priority Data

Sep. 25, 1980 [JP] Japan ................................ 55-133321

[51] Int. Cl.³ .......................................... G01N 21/72
[52] U.S. Cl. ................................... 250/563; 356/237; 250/572
[58] Field of Search ............... 250/562, 563, 560, 572; 356/444, 30, 131, 71, 39, 40, 237; 358/106

[56] References Cited

U.S. PATENT DOCUMENTS 3,280,692 10/1966 Milnes et al. ........................ 250/562
3,851,972 12/1974 Smith et al. ............................ 356/39
4,330,205 5/1982 Murakami et al. .................. 250/572

Primary Examiner—David C. Nelms
Assistant Examiner—J. Jon Brophy
Attorney, Agent, or Firm—Sughrue, Mion, Zinn, Macpeak and Seas

[57] ABSTRACT

An apparatus for detecting and measuring the area of defects in a sheet or rolled material comprises a defect detection section which rapidly scans the whole area of the material to locate the positions of defects and a defect size measuring section which is moved directly to each of the located positions to measure the area of the defect.

8 Claims, 1 Drawing Figure

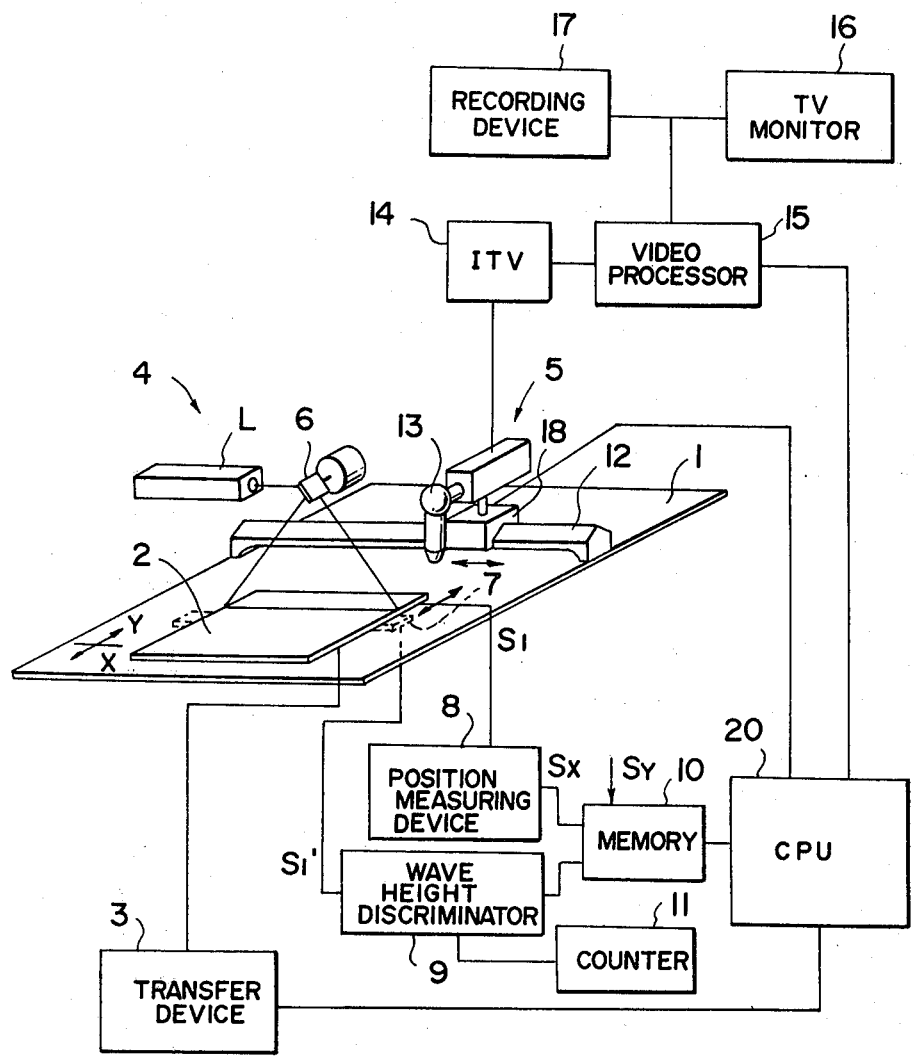

APPARATUS FOR DETECTING AND MEASURING DEFECTS

BACKGROUND OF THE INVENTION

1. Field of the Invention

This invention relates to an apparatus for detecting and measuring minute defects in sheet or rolled material and, more particularly to an apparatus for detecting and measuring defects in sheet or rolled material which is capable of highly efficient measurement of even the area of minute defects in relatively large-area sheet material or wide-width rolled material.

2. Description of the Prior Art

Pin holes, irregularities and other kinds of defects requiring detection are likely to occur in various types of films as, for example, in the thin films produced by vacuum deposition, sputtering and other methods of producing thin films in vacuo, coated films obtained by the various coating methods, or the blackened portion of a lithographic type photosensitive film after development.

As a specific example of a problem resulting from the existence of such defects there can be mentioned the case of heat mode recording media of the type wherein recording is carried out by using a laser beam or other high energy beam to melt or evaporate a metallic recording layer of high optical density formed by vacuum deposition etc. to convert the irradiated portions of the recording layer to portions of low optical density. As any pin hole or other surface defect present in such a medium will have low optical density, it will be read as a recorded portion in the read-out process even though no information has in fact been recorded on this part of the medium. On the other hand, in the case of magnetic recording medium, the presence of a pin hole not only prevents the recording of information at the position where it exists but may even disrupt the magnetic field of the surrounding portions of the medium, making accurate read-out impossible.

Because of the problems caused by such defects in recording media, a number of inspection methods have been proposed for determining whether or not recording media are suitable for use.

One such inspection method detects surface defects in the medium by using a laser beam to scan the medium in the X and Y directions. However, if this method is to be used not only for the detection of defects but also for the determination of the size and shape of minute defects, it becomes necessary to reduce the diameter of the scanning laser beam to a very small size. This in turn means that the scanning range has to be severely limited in view of the aberration of the scanning lens, the precision of the oscillating (rotating) mirror and other considerations. For example, where the size and shape of minute defects measuring only a few μm in diameter are to be determined, it becomes necessary to reduce the diameter of the laser beam so that the size of the scanning spot on the recording medium is on the order of several tens of μm. As a consequence, where an optical system of the ordinary type is used, the size of the area that can be scanned with the required degree of accuracy is four inches at the very most. Therefore, when the inspection is to be conducted in respect of a vacuum deposited thin film or other material having a relatively large area, it becomes impossible to scan the entire area in one operation and the area must be divided into a number of inspection regions for successive scanning. As the time required for scanning the entire area in this way is considerable, the inspection operation consumes much time and lacks practicability.

On the other hand, if the laser beam is used with no reduction in diameter or if a relatively large diameter beam is used with only moderate reduction, it is of course possible to carry out scanning of a large area without being limited by the precision of the optical system. In this case, however, the detection accuracy will be low and it will not be possible to determine the size or shape of the detected defects.

SUMMARY OF THE INVENTION

The object of the present invention is to provide an apparatus for detecting and measuring defects which is capable of detecting and measuring surface defects in large-area sheet material and wide-width rolled material with high accuracy and high speed.

This object is attained by providing an apparatus for detecting and measuring defects comprising a defect detection means for detecting the presence of defects in a material under inspection with high speed and a size measuring means for accurately measuring the area etc. of the defects detected by the defect detection means, the two means being functionally integrated with each other. As the defect detection means is required only to detect whether or not any defects are present in the material under inspection, there is no need to reduce the laser beam to a very small diameter, and it is therefore possible to scan a large area with the beam. As a result, the detection operation can be carried out with high speed. Meanwhile, the size measuring means need only measure those portions where defects were found to exist by the defect detection means so that wasted time is held to a minimum. Thus, by using the apparatus according to the present invention, it is possible to carry out defect detection and measurement at a high speed with no reduction in detection accuracy.

The invention will now be described with respect to a preferred embodiment of the apparatus for detecting and measuring defects.

BRIEF EXPLANATION OF THE DRAWING

The single drawing is a perspective, schematic view of an apparatus for detecting and measuring defects according to the present invention.

DESCRIPTION OF THE PREFERRED EMBODIMENT

Referring to the drawing, the material to be inspected (not shown) is placed on a mount 2 which is provided on a table 1 so as to be free to move in the Y direction as shown by an arrow. The mount 2 is, for reasons to be explained later, made of a transparent material and is moved in the Y direction by a transfer device 3 of any convenient construction.

The apparatus has a defect detection section 4 which causes a light beam to scan the whole area of a large-area sheet material placed on the table 1 so as to detect the position of any minute defects existing in the material and a defect size measuring section 5 which measures the area etc. of the minute defects detected by the defect detection section 4.

The defect detection section 4 is provided with a galvanometer mirror 6 situated above the mount 2. The galvanometer mirror 6 directs the laser beam from a laser beam source L onto the material under inspection (for example, a sheet of the heat mode recording medium mentioned earlier) which has been placed on the mount 2 and causes the laser beam to scan the material in the X direction as also indicated by an arrow. Therefore, by the operations performed by the mount 2 and the galvanometer mirror 6, the whole area of the material is scanned two-dimensionally, namely in the X and Y directions. As the laser beam source L there can be used, for example, an He-Ne laser that produces a laser beam with a diameter of about 1 mm. Before being directed onto the material under inspection, the laser beam is condensed to a diameter between several hundred μm and 100 μm by a condenser optical system (not shown).

When the laser beam comes to a pin hole or other defect in the material, it transmits through the defective portion. A photoreceptor 7 is provided on the opposite side of the transparent mount 2 in order to detect this transmitted light. For this photoreceptor 7 there is used a combination of a CCD, photodiode array or optical fiber photoreceptor and a photomultiplier. Upon receiving light transmitted through a defective portion of the material, the photoreceptor 7 outputs a time series signal $S_1$. The photoreceptor 7 is connected to a wave height discriminator 9. A position measuring device 8 is input with the time series signal $S_1$ indicative of the position of the laser beam on the material under inspection and, by means of circuitry not shown in the drawing, determines the position of the laser beam on the X axis on the basis of this signal $S_1$ and outputs an X-axis signal $S_x$ in accordance with the determined position. A signal $S_y$ indicating the Y-axis position of the defect is, on the other hand, obtained for example by counting the number of driving pulses of a pulse motor for driving the mount 2. Time series X - Y signals derived from the signals $S_x$ and $S_y$ are then stored in a memory circuit 10.

In order to eliminate noise, the wave height discriminator 9 receives from the photoreceptor 7 a signal $S_1'$ corresponding to the time series signal $S_1$ fed to the position measuring device 8 and functions to recognize a signal as a detection signal only when it corresponds to more than a prescribed amount of light received by the photoreceptor 7. In this way it is determined whether or not a signal produced as a result of light received by the photoreceptor 7 is truly indicative of a defect in the material. Those signals which are found to be based on defects are counted by a counter 11. Alternatively, the wave height discriminator may be arranged to discriminate among two or more levels of the time series pulses of the signal $S_1'$ from the photoreceptor 7 and to have the discriminated components counted separately for each level by the counter 11. When this type of wave height discrimination is carried out, it also becomes possible to make a rough estimation of defect size. Since, as mentioned above, the wave height discriminator is connected to the memory circuit 10, the memory circuit 10 is caused to store defect position signals in correspondence with the aforesaid X - Y signals.

Another possible arrangement is to have the position measuring device 8 connected to the photoreceptor 7 and to detect position signals only at those times when there is an input from the photoreceptor 7.

The defect size measuring section 5 has a microscope 13 for observing defects in the material under inspection. The microscope 13 is mounted on a rail 12 extending over the table 1 in the X direction and is made freely slidable in the X direction. In order to convert the image within its field of view into time series signals, the microscope 13 is connected to an industrial TV unit (ITV) 14. The output terminal of the ITV 14 is connected to a video processor 15 which determines the size and shape of defects on the basis of the data output by the ITV 14. The video processor 15 also converts the output of the ITV 14 into picture signals which are fed to a TV monitor 16 for producing a picture corresponding to the image being picked up by the microscope 13. Although not absolutely essential, it is also preferable to connect the output terminal of the video processor 15 to a recording device 17 for recording the output from the processor. The microscope 13 is moved in the X direction along the rail 12 by a transfer device 18 of any appropriate structure.

The defect size measuring section 5 just described is functionally integrated with the previously described defect detection section 4 via a central processing unit (CPU) 20 and the memory circuit 10.

The CPU 20 is connected to the memory circuit 10 from which it receives coordinate system signals $S_x$, $S_y$ indicating the position of defects. The CPU 20 uses the Y-axis signal $S_y$ to control the mount transfer device 3 so as to move the mount 2 in the Y direction and uses the X-axis signal $S_x$ to control the microscope transfer device 18 so as to move the microscope 13 in the X direction. In this way the CPU 20 controls the relative positions of the material being inspected and the microscope 13 so as to cause a given defect to come within the field of the microscope 13. Following this, the CPU 20 controls the video processor 15 to carry out measurement of the defect size etc., thus completing the detection and measurement operation for one defect in the material. The CPU 20 then proceeds to control the steps for the size measurement for the remaining defects and, after all the detected defects have been measured, to issue a comand for replacing the inspected sheet of material with the next one to be inspected.

If the method described above of using the wave height discriminator 9 to carry out a rough size measurement is used, then the precise measurement using the microscope 13 can be limited to those detected defects known to be larger than a certain size from the results of the rough measurement. This is particularly convenient where there is a time limitation since it makes it possible to complete the measurement of defects within a fixed time alloted for the overall operation.

In cases where there is a danger that the image picked up by the microscope 13 will be out of focus because of tilting of the material under inspection or some other cause, it is advisable to use a microscope capable of autofocusing and to have the focal length controlled automatically by the CPU 20.

In the above described embodiment, the defect size measuring section is of the type which uses a microscope. The invention is not, however, limited to use of this type of size measuring section and can employ any type of measurement section whatever including, by way of example, one in which the size of defects is measured by scanning the material with a laser beam having a small diameter of about 10 μm.

It should be noted that when the apparatus according to the present invention is used for the detection of defects in a heat mode recording medium, the intensity of the scanning laser beam must be lower than the sensitivity level of the recording medium.

The embodiment described above relates to an apparatus for detecting and measuring the size of defects in a sheet material. It is, however, also possible to detect and measure the size of defects in a rolled material by first detecting the position of the defects in the rolled material as it is transported through the defect detection section and thereafter measuring the size of the defects utilizing the position information so obtained. In this case, it may sometimes happen that the size measurement will proceed more slowly than the defect detection, but this problem can be eliminated or at least alleviated by setting an upper limit on the permissible number of defects per unit area of the material and not submitting any portion of the material having a higher number of defects to scanning by the defect size measuring section on the understanding that such regions will be discarded. Moreover, as it is not absolutely necessary for the rolled material to be transported between the defect detection section and the defect size measuring section continuously, the problem of the difference in processing speeds can be overcome by allowing the material to form loops between the two sections.

As is clear from the foregoing description, the present invention makes it possible to carry out defect detection and size measurement with high speed and precision by subjecting the whole area of the material under inspection to high speed defect detection in a defect detection section, storing the information obtained in the defect detection section regarding the position of the defects and using this stored information to move a microscope or the like in the defect size measuring section directly to the position of the defect to be measured. As a consequence, the invention makes it possible to reduce the amount of time required for high precision defect detection to much below that required heretofore.

We claim:

1. An apparatus for detecting and measuring defects comprising a defect detection means for detecting the position of minute defects in the material under inspection, means for scanning the material with a light beam, means for generating position information regarding the minute defects detected by the detection means, a defect size measuring means for measuring the area of the minute defects detected by the defect detection means, memory means for storing the position information regarding the minute defects detected by the defect detection means, and operating means, for using the position information stored by the memory means, to move the defect size measuring means to the position for measuring the defects.

2. The apparatus according to claim 1, wherein the light beam is a laser beam.

3. The apparatus according to claim 1 or 2, wherein the means for measuring the area of the minute defects includes a microscope.

4. The apparatus according to claim 3, wherein the microscope is connected to an industrial TV unit and a video processor for determining the area of the defects.

5. The apparatus according to claim 1 or 2, wherein the means for measuring the area of the minute defects includes a laser beam scanner with a beam of a diameter not exceeding $10\mu$.

6. The apparatus according to claims 1 or 2, wherein the operating means includes a central processing unit.

7. The apparatus according to claims 1 or 2, wherein a wave height discriminator is further provided between the defect detection means and the memory means, whereby the position information stored by the memory means is limited to that relating to defects of greater than a predetermined size.

8. The apparatus according to claims 1 or 2, wherein a wave height discriminator is further provided between the defect detection means and the memory means, whereby the position information stored by the memory means is limited to that relating to defects of greater than a predetermined size and the stored information is classified according to the strength of the position information outputted by the defect detection means to provide a rough measurement of defect size.

* * * * *